United States Patent [19]

Bailey et al.

[11] Patent Number: 5,432,092
[45] Date of Patent: * Jul. 11, 1995

[54] C-TERMINAL PEPTIDE SEQUENCING USING DIPHENYL PHOSPHOROISOTHIOCYANATIDATE AND PYRIDINE

[75] Inventors: Jerome M. Bailey, Duarte; John E. Shively, Arcadia, both of Calif.

[73] Assignee: City of Hope, Duarte, Calif.

[*] Notice: The portion of the term of this patent subsequent to Jan. 19, 2010 has been disclaimed.

[21] Appl. No.: 94,024

[22] PCT Filed: Feb. 7, 1992

[86] PCT No.: PCT/US92/01009

§ 371 Date: Jul. 26, 1993

§ 102(e) Date: Jul. 26, 1993

[87] PCT Pub. No.: WO93/11436

PCT Pub. Date: Jun. 10, 1993

Related U.S. Application Data

[63] Continuation-in-part of Ser. No. 801,944, Dec. 3, 1991, Pat. No. 5,180,807.

[51] Int. Cl.⁶ .................. G01N 33/68; C07K 1/00
[52] U.S. Cl. ............................... 436/89; 530/402; 530/427
[58] Field of Search ............ 436/89, 161; 530/345, 530/402, 427

[56] References Cited

U.S. PATENT DOCUMENTS

| | | | |
|---|---|---|---|
| 4,837,165 | 6/1989 | Hawke | 436/89 |
| 5,041,388 | 8/1991 | Boyd et al. | 436/89 |
| 5,049,507 | 9/1991 | Hawk et al. | 436/89 |
| 5,180,807 | 1/1993 | Bailey et al. | 530/345 |

OTHER PUBLICATIONS

Kenner, G. W. et al., J. Chem. Soc. 673-678 1953.

*Primary Examiner*—David A. Redding
*Attorney, Agent, or Firm*—Edward S. Irons

[57] ABSTRACT

A carboxy terminal protein sequencing process is disclosed which utilizes phosphoroisothiocyanatidate for the derivatization step.

5 Claims, 7 Drawing Sheets

C-TERMINAL PEPTIDE SEQUENCING USING DIPHENYL PHOSPHOROISOTHIOCYANATIDATE AND PYRIDINE

This application is a continuation-in-part of Bailey application Ser. No. 07/801,944 filed Dec. 3, 1991, now allowed U.S. Pat. No. 5,180,807.

FIELD OF THE INVENTION

This invention relates to a method, which may be automated, for the C-terminal sequencing of peptides in which a novel combination of reagents is utilized. More particularly, the invention relates to C-terminal peptide sequencing with a reagent comprising diphenyl phosphoroisothiocyanatidate and pyridine.

BACKGROUND OF THE INVENTION

A. The Prior Art

The large number of cloned gene products and the widespread use of DNA sequencing to determine the primary structure of peptides, has increased the need for carboxy-terminal (C-terminal) sequencing. C-terminal sequencing complements existing N-terminal degradations based on Edman chemistry (Edman, P. Acta. Chem. Scand. 4:283–293 (1950)). Although many methods have been proposed (see Rangarajan, M., Chemical methods of amino acid sequence analysis from carboxy terminal end. In Protein/Peptide sequence Analysis: Current Methodologies (Brown, A. S., Ed.) pp. 135–144, CRC Press, Boca Raton, Fla. (1988) and Ward, C. W., Carboxyl terminal sequence analysis. In Practical Protein Chemistry—A Handbook (Darbre, A., Ed.) pp. 491–525, John Wiley and Sons, Ltd. (1986)) the thiocyanate method, first described by Schlack and Kumpf, Z. Physiol. Chem. 154:125–170 (1926), has been the most widely studied and the most attractive because of its similarity to the Edman degradation. This method involves reaction of a protein or peptide with isothiocyanate reagents, in the presence of acetic anhydride, to form a C-terminal thiohydantoin amino acid. The derivatized amino acid is then hydrolyzed to yield a shortened polypeptide and a thiohydantoin amino acid. As the thiohydantoin amino acids have similar UV absorption spectra and equivalent extinction coefficients as the phenylthiohydantoin amino acids formed during the Edman degradation, the sensitivity of the thiocyanate method is expected to be similar to that of current N-terminal methods (10–200 pmol, 20–30 cycles). Historically, the main disadvantages of this procedure have been the severity of the conditions required for complete derivatization of the C-terminal amino acid and for hydrolysis of the derivatized amino acid to yield a shortened peptide and thiohydantoin derivative. Although several groups have tried to reduce the severity of the hydrolysis conditions (Waley, et al. J. Chem. Soc. 1951:2394–2397 (1951); Kjaer, et al. Acta Chem. Scand. 6:448–450 (1952); Turner, et at. Biochim. Biophys. Acta. 13:553–559 (1954), it was not until the introduction of acetohydroxamate (Stark, G. R. Biochemistry 7:1796–1807 (1968) as a mild and rapid cleavage reagent, that the hydrolysis problem appeared solved. The introduction of trimethylsilylisothiocyanate (TMS-ITC) (see U.S. Pat. No. 4,837,165) improved the yield of thiohydantoin formation and reduced the number of complicating side products. The repetitive yields were low, limiting the number of degradation cycles to 2 or 3 residues. Certain amino acids were reported to be unable to form thiohydantoins (Hawke, et al. Anal. Biochem. 166:298–307 (1987); Miller, et al., Techniques in Protein Chemistry (Hugli, T. E., Ed.) pp. 67–78, Academic Press, Inc. (1989)).

Recent work, Bailey, et al. Biochemistry 29:3145–3156 (1990), found that hydrolysis with acetohydroxamate led to the formation of a shortened peptide with a stable hydroxamate ester at the C-terminus, thereby preventing further degradation and explaining the low repetitive yields obtained with this reagent (Miller, supra; Meuth, et al., Biochem. 21:3750–3757 (1982)). Hydrolysis with dilute aqueous triethylamine was found to lead to the quantitative formation of a thiohydantoin amino acid and a shortened peptide capable of continued degradation. Additional work (Bailey, supra) addressed the generality of the thiocyanate method by examining the reaction of TMS-ITC with model peptides containing most of the naturally occurring amino acids. Problems were identified when Pro, Asp, Glu, Thr, and Asn were encountered during the degradation. Minimization of the reaction time with acetic anhydride was found to allow the quantitative degradation of Glu and Thr and addition of a nucleophile prior to derivatization by TMS-ITC was used to allow partial degradation of C-terminal Asp.

Automation of C-terminal chemistry has been attempted by several groups. Application of this chemistry to the solid phase (polypeptides covalently attached to a solid support) has been recognized to facilitate the successful automation of this chemistry. The advantages of covalently immobilizing a polypeptide to a solid support include: elimination of sample washout thereby resulting in high initial and repetitive yields, the ability to use reagents and solvents optimal for derivatization and washing, and the ability to efficiently wash the sample to remove reaction by-products resulting from thiohydantoin formation, thereby creating a potential for a low chemical background.

The concept of solid phase sequencing for N-terminal Edman chemistry was first proposed by Laursen, R. A. Eur. J. Biochem 20:89–102 (1971), and has since been used successfully by a number of groups for the Edman degradation (Laursen, et al. FEBS Lett. 21:67–70 (1972); L'Italien, et al. Anal. Biochem. 127:198–212 (1982); L'Italien, Methods in Protein Microcharacterization, (Shively, J. E., Ed.) pp. 279–314, Humana Press, Inc. (1986)). Initial attempts at C-terminal sequencing using the thiocyanate chemistry from covalently attached peptides was made by several groups. Williams, et al. FEBS Lett. 54:353–357 (1975) were able to perform 1–3 cycles on peptides (1 μmol) covalently attached to N-hydroxysuccinimide activated glass beads using 12N HCl for cleavage of the peptidylthiohydantoins. Utilizing this same procedure, Rangarajan, et al. Biochem. J. 157:307–316 (1976) were able to perform six cycles on ribonuclease (1 μmol) covalently coupled to glass beads with a cycle time of 5 to 6 hours. Three successful cycles, with HPLC identification of the released amino acid thiohydantoins, were performed by Meuth et al. Biochem. 21:3750–3757 (1982) on a 22-amino acid polypeptide (350 nmol) covalently linked to carbonyldiimidazole activated aminopropyl glass. These authors used thiocyanic acid for derivatization to a peptidylthiohydantoin and acetohydroxamate for cleavage further reducing the time per cycle to 3 hours. A more recent report by Inglis et al., Methods in Protein Sequence Analysis (Wittmann-Lebold, B., Ed.) pp. 137–144, Springer-Verlag (1989) reports the sequential degradation of nine residues from a synthetic decapeptide (30 nmol) covalently coupled to glass beads with a cycle time of 48 min., however no experimental details were given.

Early work concerning the automation of the thiocyanate chemistry for the purpose of carboxy-terminal sequencing of proteins and peptides revealed several problems: (1) cleavage of the peptidylthiohydantoin with acetohydroxamate resulted in a shortened peptide blocked to further sequence degradation from the C-terminus due to the formation of a stable hydroxamate ester, (2) although cleavage of the peptidylthiohydantoin with dilute aqueous triethylamine does not result in the formation of a blocked shortened peptide, the use of aqueous solutions on peptides covalently bound to polyvinyldifluoride (PVDF) was found to inadequately "wet" the support and cleavage did not occur (50° C.) or only very slowly at elevated temperatures (70° C.). The inclusion of 30% water miscible organic solvent to the dilute triethylamine solution was found to allow adequate "wetting" of the membrane support, but significantly inhibited the cleavage reaction (Bailey, et al., Carboxy terminal sequencing: Automation and application to the solid phase, Techniques in Protein Chemistry: II (Villafranca, J. J., Ed.) pp. 115–129, Academic Press, Inc. (1991), (3) the activation of the C-terminal carboxylic acid with acetic anhydride was found to prevent or contribute to the reduced yields of sequencing on certain of the twenty naturally occurring amino acids (Bailey, et al., supra (1990), e.g., threonine, serine, aspartate, glutamate, and proline.

The cleavage problems were solved with the introduction of a new reagent, sodium trimethylsilanolate, for cleavage of the covalently coupled peptidylthiohydantoins and the introduction of a carboxylic acid modified polyethylene support for covalent attachment of the peptide sample (see, e.g., patent application PCT/US90/02723). This novel cleavage reagent was found to hydrolyze specifically the peptidylthiohydantoin into a shortened peptide capable of continued sequencing from the C-terminus and a thiohydantoin amino acid. The thiohydantoin amino acids are then identified by HPLC.

B. Derivatization of the C-Terminal Amino Acid

The thiocyanate chemistry for C-terminal sequencing can be deemed to consist of two separate parts, (1) the derivatization of the C-terminal amino acid to form a thiohydantoin, and (2) the specific cleavage of that c-terminal thiohydantoin to form a shortened peptide capable of continuing degradation and a thiohydantoin amino acid.

Although the derivatization of amino acids to the corresponding thiohydantoins has been studied since this reaction was first reported in 1911 (Johnson, et al. *J. Am. Chem. Soc.* 33:1973–1978 (1911)), the mechanism of peptidylthiohydantoin formation by acetic anhydride and thiocyanate ions is still not well understood. Early experiments confirmed the assumption that thiocyanic acid is first formed when acetic anhydride and acetic acid interact with ammonium thiocyanate and it is the thiocyanic acid which actually reacts to form the thiohydantoin (Johnson, et al., *J. Am. Chem. Soc.* 35:1136–1143 (1913)). The differing ability of the various salts of thiocyanic acid to form a thiohydantoin was reasoned to result from their ability to form thiocyanic acid on interaction with acetic anhydride and acetic acid (Johnson, et al. *J. Am. Chem. Soc.* 37:2406–2416 (1915). When more convenient methods for the preparation of thiocyanic acid became available, thiocyanic acid, in the presence of acetic anhydride, was found to be more reactive for the formation of 2-thiohydantoins than were the thiocyanate salts. As a result, thiocyanic acid has been used by Kubo, et al., *Chem. Pharm. Bull.* 19:210–211 (1971) and more recently by Inglis, et al., supra (1989) for the sequential degradation of peptides from the C-terminus. However, one of the principal drawbacks of thiocyanic acid is that it tends to be self reactive, even at ambient temperature, and quickly loses its ability to derivatize the peptide. Furthermore, these polymeric thiocyanic acid products are intensely UV absorbing at the wavelengths used for thiohydantoin detection and can subsequently interfere with the HPLC identification of the released thiohydantoin amino acid. The instability of the free thiocyanic acid presents difficulties when the chemistry is automated, which requires reagents stable to storage in a reagent bottle at room temperature. As discussed by Inglis, et al., C-terminal sequence analysis, Met. Protein Sequence Analysis (Jornvall/Hoog/Gustavsson, Eds.) pp. 23–34, Birkhauser-Verlag, Basel (1991), one way to facilitate stabilization of the thiocyanic acid is to refrigerate it while in the automated instrument. A less costly and more convenient solution to the problems caused by the use of thiocyanic acid involves the use of trimethylsilylisothiocyanate (TMS-ITC) for derivatization of the C-terminal amino acid to a thiohydantoin (see, U.S. Pat. No. 4,837,165). Consistent with the observation that silylated amines have often been found to be better nucleophiles than the corresponding unsubstituted amines (Fleming, I., Comprehensive Organic Chemistry, Vol. 3 (Jones, D. N., Ed.) pp. 541–686, Pergamon Press (1979)), the trimethylsilyl group offered two advantages, (1) it stabilized the thiocyanate sufficiently so that self-reaction was no longer a problem, and (2) it did not compromise the ability of the thiocyanate to form thiohydantoins.

The intermediate involved in thiohydantoin formation has been a subject of study for many years. An oxazolinone was postulated to be a necessary intermediate during the synthesis of amino acid thiohydantoins with acetic anhydride and ammonium thiocyanate when this reaction was first studied (Johnson, et al., *J. Am. Chem. Soc.* 35:1136–1143 (1913)). The racemization of the C-terminal amino acids observed on reaction with acetic anhydride and TMS-ITC (Bailey, supra (1990)) suggests that reaction of peptides with acetic anhydride forms a peptide oxazolinone. This is consistent with the above postulated mechanism. The formation of oxazolinones is known to cause racemization of amino acids (Csonka, et al. *J. Biol. Chem.* 99:213–216 (1933); Carter, et al., *J. Biol. Chem.* 133:117–128 (1940); Goodman, et al. *J. Am. Chem Soc.* 86:2918–2922 (1964)). Further evidence of an oxazolinone intermediate during the formation of amino acid thiohydantoins was obtained by Csonka, et al. supra. Additional studies described by Cornforth, J. W., The Chemistry of Penicillin, pp. 688–848, Princeton University Press (1949) actually demonstrated the formation of an oxazolinone intermediate in the formation of thiohydantoins by the combined use of absorption spectra and polarimetry to follow the rate of oxazolinone formation. In fact, once the oxazolinone was formed, the reaction with isothiocyanic acid was found to be facile enough to occur readily at 0° C. in the case of 2-phenyl-4-benzly-5-oxazolinone (Cornforth (1949), supra).

Activation of the carboxylic acid is typically done in the presence of the thiocyanate reagent. Acetic anhydride, first used by Johnson and Nicolet (1911), supra, has been the most commonly used reagent and is still the reagent of choice. Propionic anhydride was also found to be as effective as acetic anhydride for activation, while benzoic anhydride was found to be uneffective (Johnson, supra, (1915)). Kubo, et al. *Chem. Pharm. Bull.* 19:210–211 (1971) also found acetyl chloride to be effective for activation. Woodward's reagent K (Woodward, et al. *Tetrahedron, Suppl.* 7:415–440 (1986)) was recently shown to be an effective activating agent (Hawke, et al., *Tetrahedron Letters* 31:3849–3852 (1990)). Dicyclohexylcarbodiimide was also shown by applicants to be capable of forming an activated carboxylic group suitable for reaction with TMS-ITC to form a thiohydantoin in good yield. The common link between all of these activating reagents is that they are all capable of forming an oxazolinone on the C-terminus of a protein or peptide.

Recent work examined the reaction of acetic anhydride and TMS-ITC with model peptides containing most of the naturally occurring amino acids at the C-terminus (Bailey, et al., supra (1990)). It was found that the reaction between acetic anhydride and TMS-ITC could be separated and each step performed independent of the other. Problems were identified with glutamate, aspartate, threonine, and proline. All of these problems occurred on the activation step with acetic anhydride. Both glutamate and aspartate rapidly form a cyclic anhydride in the presence of acetic anhydride which is not reactive with TMS-ITC or the thiocyanate salts. In the case of glutamate, the kinetically favored 5-membered oxazolinone ring, capable of reaction with TMS-ITC, initially forms, but is rapidly converted into the more thermodynamically stable 6-membered cyclic anhydride which is not capable of reaction with TMS-ITC. Because the oxazolinone is initially formed, a minimum reaction time with acetic anhydride can make possible up to 80% derivatization of C-terminal glutamate to a thiohydantoin (Bailey, et al., supra (1990)).

Formation of the cyclic anhydride in the case of C-terminal aspartic acid is so rapid that no formation of thiohydantoin aspartate could be detected during manual solution phase sequencing (Bailey, et al., supra (1990)). Aspartate is known to form a cyclic anhydride which is not reactive to thiocyanate on reaction with acetic anhydride (Nicolet, B. H., *J. Amer. Chem. Soc.* 52:1192–1195 (1930); Swan, J. M. *Nature* 169:826–828 (1952); Barker, C. C., *J. Chem. Soc.* 453–456 (1953); Stark, G. R. *Biochemistry* 7:1796–1807 (1968)).

It is postulated that the formation of the oxazolinone of C-terminal aspartate, required for thiohydantoin formation, is the initially favored reaction with acetic anhydride, but once formed, rapidly rearranges to the more thermodynamically stable five-membered cyclic anhydride which is not capable of reaction with TMS-ITC. Threonine on reaction with acetic anhydride readily forms an oxazolinone which is capable of reaction with TMS-ITC to form a thiohydantoin, but this oxazolinone can readily dehydrate at its side chain hydroxyl group to form an unsaturated oxazolinone, which is not capable of reaction with TMS-ITC. Proline due to its tertiary amino group, is not capable of forming an oxazolinone (Matsuo, et al., *Biochem. Biophys. Res. Comm.* 22:69–74 (1966); Holcomb, et al. *Biochemistry* 4:1291–1296 (1968)), so any reaction with TMS-ITC would have to be through a linear mixed anhydride intermediate. The fact that TMS-ITC does not react with the cyclic anhydride formed when aspartic acid is at the C-terminus of a peptide (Bailey, supra (1990)), suggests that TMS-ITC may not be able to react with the mixed anhydride formed when proline is at the C-terminus.

An isothiocyanate reagent capable of specific reaction with the carboxylic acid at the C-terminus of a protein or peptide in the absence of activation with acetic anhydride would provide a means to solve some of the problems outlined above. In particular, such a reagent would potentially be able to improve the yields obtained when amino acids such as glutamate, aspartate, threonine, or proline are encountered in a sequential degradation from the C-terminus of a protein or peptide. Such a reagent is phosphoroisothiocyanatidate. This reagent was first synthesized and proposed (as diphenyl phosphoroisothiocyanatidate) for use in C-terminal sequencing by Kenner, et al. *J. Chem. Soc.* 673–678 (1953). The main drawback is its slow reaction time to form a thiohydantoin amino acid. As shown by Kenner, et al., this reagent in the presence of triethylamine takes 110 hours to quantitatively form a thiohydantoin amino acid.

SUMMARY OF THE INVENTION

This invention provides a novel method for C-terminal sequencing of peptides. Preferably the peptide to be sequenced is attached covalently to a derivatized support such as carboxylated polyethylene (PE-COOH). The C-terminal carboxylic acid group is first converted to a carboxylate which is then reacted with diphenyl phosphoroisothiocyanatidate. The phosphoryl moiety of the reaction product is removed by reaction with pyridine. Cleavage is accomplished with trimethylsilanolate in methanol.

DETAILED DESCRIPTION OF THE INVENTION

Application Ser. No. 07/801,944 now U.S. Pat. No. 5,180,807; describes and claims a process for the carboxy terminal sequencing of a peptide with a combination of phosphoroisothiocyanatidate and pyridine in a solvent such as acetonitrile. Example I of that application illustrates the invention as applied to a peptide free in solution. In Example II, the peptide is covalently attached to PE-COOH. The pyridine is present in slight excess with respect to the concentration of phosphoroisothiocyanatidate to facilitate formation of a carboxylate salt of the peptide.

Pursuant to this invention, the pyridine and phosphoroisothiocyanatidate reagents are used sequentially. In a first step, pyridine or similar base converts the peptide which is bound to a solid phase, to a carboxylate salt. In a second step, the carboxylate is reacted with the phosphoroisothiocyanatidate reagent. Sequential reaction first with pyridine and then with phosphoroisothiocyanatidate permits sequencing through Asp or Glu.

Further, separation of these steps eliminates the need for an excess of pyridine.

Peptide samples are first covalently attached to a membrane preferably PE-COOH. Procedures for such covalent attachment is described in applications Ser. No. 07/801,944 (U.S. Pat. No. 5,180,807) and copending Ser. No. 07/576,943, each incorporated herein by reference.

Step 1: The peptide sample is converted to a carboxylate, preferably by reaction with an amine. Water or organic solutions containing from about 1.0 to about 60% by weight of an amine are appropriate. Solutions of tertiary amines in anhydrous organic solvents are appropriate. A 5% solution of triethylamine in water is effective. A 40% to 60% by volume solution of triethylamine in methanol is preferred.

Other tertiary amines, such as diisopropylethylamine, secondary amines, primary amines, sodium and potassium hydroxide are also effective. The advantage of using a tertiary amine in an anhydrous organic solvent, such as methanol, is that during the repetitive derivatization treatments used in an automated instrument the derivatized thiohydantoin amino acid will not be cleaved. (Bailey, J. M., and Shively, J. E. "Carboxy terminal sequencing: Automation and application to the solid phase" *Techniques in Protein Chemistry: II* (Villafranca, J. J., Ed.) pp. 115-129, Academic Press, Inc. (1991)).

Aqueous solvents may result in cleavage of the already derivatized amino acid with a consequent reduced sequencing yield. This cleavage will occur at the * in the following scheme:

Cleavage will also occur if a primary or secondary amine is used, but with consequent reduced yield of sequencing results. Use of a primary or secondary amine may, on cleavage, yield a stable amide resulting in a peptide blocked to further sequencing.

Use of sodium or potassium hydroxide in a mixture of organic and aqueous solvent may also result in unwanted early cleavage and thereby reduce the yield of sequencing.

Figure 1:
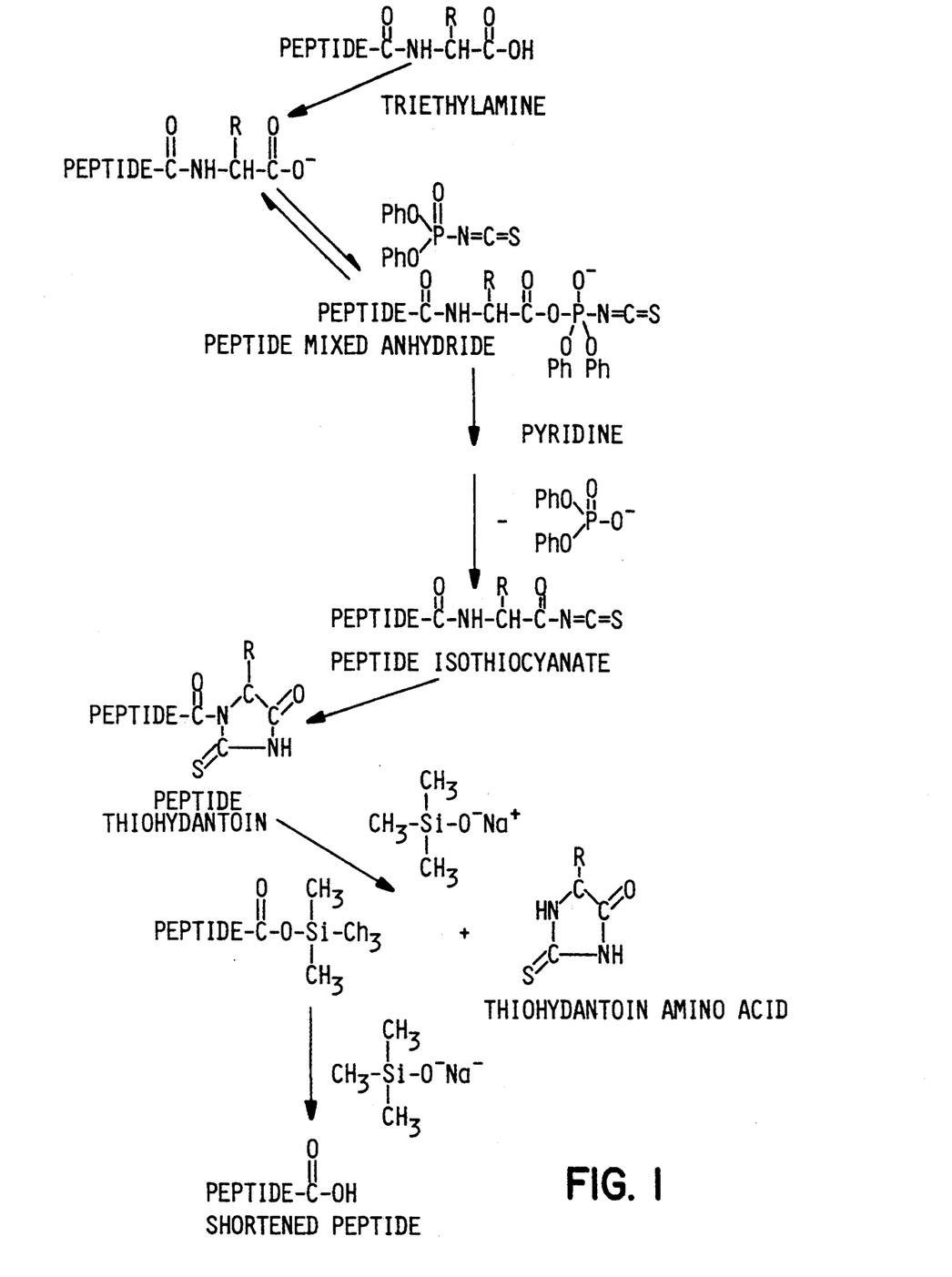
FIG. 1 illustrates the chemistry involved in the method of the invention.

Step 2: The second step involves reaction of the C-terminal carboxylate product of step 1 with diphenyl phosphoroisothiocyanatidate. The original mechanism discussed by Khorana (Kenner, G. W., Khorana, H. G., Stedman, R. J. *J. Chem Soc.* 673-678 (1953)) suggests an equilibrium reaction of the diphenyl phosphoroisothiocyanatidate reagent with the C-terminal carboxylate to produce free a isothiocyanate ion which can then attack the activated phosphoryl-carboxylate to produce a thiohydantoin. Thiohydantoin formation is not reversible and therefore pulls the equilibrium toward thiohydantoin formation. The total time for complete reaction was determined by these authors to be 110 hours. Applying this chemistry to the solid phase, it has been discovered pursuant to this invention, that the mechanism proposed by Khorana may be incorrect. The mechanism shown in FIG. 1 is deemed to be more accurate. The reaction of the diphenyl phosphoroisothiocyanatidate with the C-terminal carboxylate is an equilibrium, but the isothiocyanate is not removed. This was proven by first reacting with the phosphoryl reagent, blowing out the reagent, rinsing with 2% pyridine and then reacting with 2% pyridine in acetonitrile. If the isothiocyanate ion was released as first proposed by Kenner, et al., supra, a C-terminal thiohydantoin would not have formed. The proposal that the reaction between the C-terminal carboxylate is an equilibrium was suggested by the observation that higher concentrations of diphenyl phosphoroisothiocyanatidate are more effective in forming a C-terminal thiohydantoin in good yield. In the preferred practice of the invention 1M solution of diphenyl phosphoroisothiocyanatidate in acetonitrile is used. Other solvents may be equally as effective. It is also preferred that multiple treatments, preferably automated, of the peptide with TEA/diphenylphosphoroisothiocyanatidate/pyridine be used to insure shifting the equilibrium toward formation of the derivatized carboxylic acid. An automated program is currently repeating this series of steps (TEA/diphenylphosphoroisothiocyanatidate/pyridine) three times. Temperatures from 15° C. to 90° C. may be used. 70° C. is preferred.

Step 3: A novel aspect of this chemistry is the function of pyridine or a similar amine. Pyridine rapidly catalyzes removal of the phosphoryl moiety from the Step 2 reaction product. As FIG. 1 generally indicates, concerted mechanism generates an acyl isothiocyanate which rapidly cyclizes to form a thiohydantoin amino acid. Pyridine may be used per se or in an organic solvent solution. The pyridine concentration may range from about 0.1% by volume to 100% pyridine. Acetonitrile is a preferred solvent. Lower pyridine concentrations yield cleaner chromatograms. Solvents other than acetonitrile, such as dimethyl formamide, hexanes, benzene, toluene, etc., may be used. Temperature in Step 3 may range from 15° C. to 90° C.

Step 4: Cleavage of the Step 3 peptidylthiohydantoin product is accomplished in Step 4 with sodium trimethylsilanolate, preferably in a 50% solution of methanol and tert-butanol in the manner described in application PCT/US90/02723 incorporated herein by reference. The concentration of reagent is preferably 0.1M. Treatment of the peptidylthiohydantoin with sodium trimethylsilanolate initially produces a thiohydantoin, which is analyzed by reverse phase HPLC, and a shortened peptide with a silylated C-terminal carboxylic acid group. The free carboxylate is regenerated by a second treatment with sodium trimethylsilanolate as shown in FIG. 1. Other salts of the trimethylsilanolate ion are equally effective, such as potassium trimethylsilanolate. Other plausible salts include all of the monovalent cations such as $Li^+$, $Rb^+$, $Cs^+$, $Fr^+$. The trimethyl group may be substituted with other alkyl groups or phenyl groups. The temperature of this reaction may range from 15° C. to 90° C.

EXEMPLIFICATION OF THE INVENTION

Figure 2:
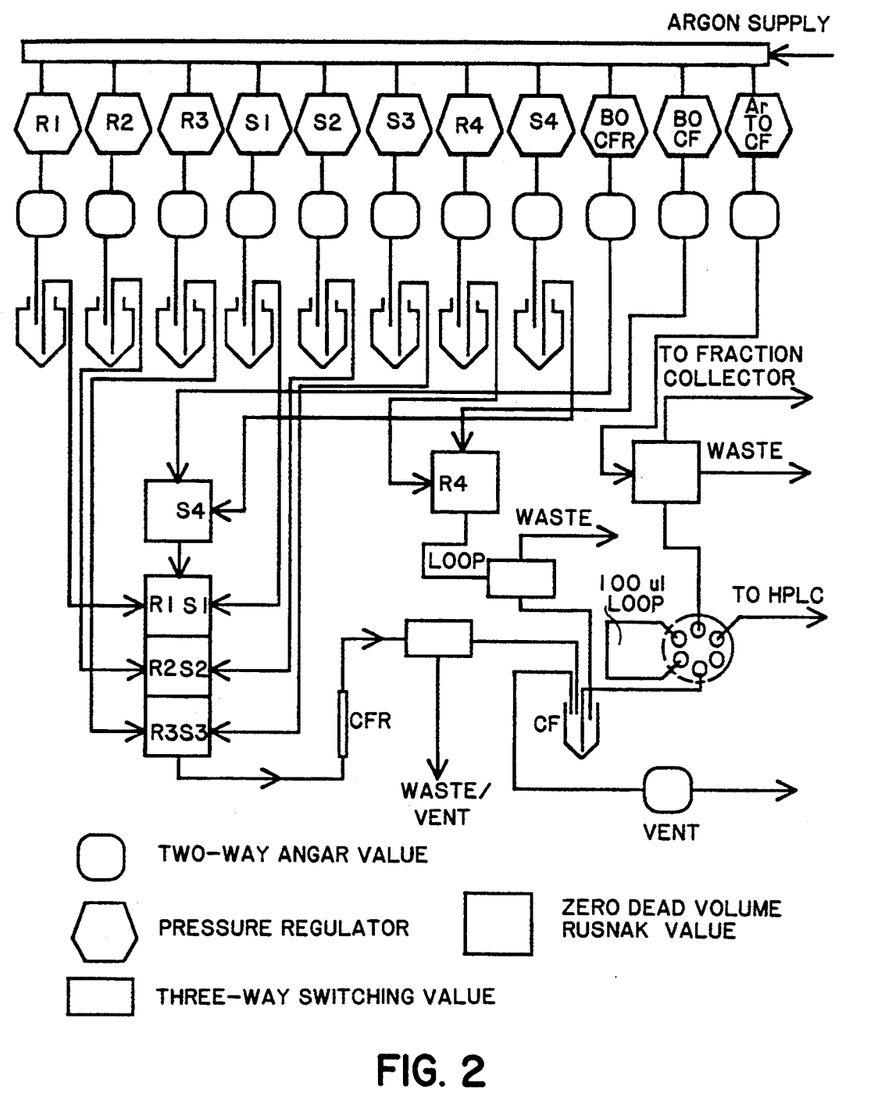
FIG. 2 is a schematic of a C-terminal sequencer useful in the practice of the invention.

This example describes the sequencing of YGGFL in four cycles utilizing a computer automated C-terminal sequencer as depicted by FIG. 2.

COVALENT COUPLING OF PEPTIDES TO CARBOXYLIC ACID MODIFIED POLYETHYLENE FILM

Samples of PE-COOH film were treated with an 1N solution of HCl for 1-2 minutes at room temperature, in order to convert the surface carboxylic acid groups to the free acid form, prior to the covalent attachment of peptide samples.

The strips of PE-COOH film (1 × 12.5 mm) were then activated by an excess of DCC (dicyclohexylcarbodiimide) in anhydrous DMF (1 g/1 ml) for 1 hour at room termperature. At the end of the activation reaction, the excess reagent was removed by rinsing the strips with anhydrous DMF. Each activated PE-COOH strip was inserted into a continuous flow reactor (CFR) (Shively et al., 1987) containing a 100 μl solution of leucine enkephalin in 50% aqueous DMF overnight at 22° C. The microbore tubing on one end of the CFR was sealed by heating and then pinched closed with pliers. After the coupling reaction, the support was rinsed with coupling solvent and acetonitrile, and then dried in a vacuum centrifuge.

| COMPOSITION OF REAGENTS AND SOLVENTS | |
|---|---|
| R1 | 50% Triethylamine in methanol |
| R2 | Diphenyl phosphoroisothiocyanatidate in acetonitrile |
| R3 | 0.10M Sodium trimethylsilanolate in 50% methanol, 50% t-butyl alcohol |
| [R4 | No R4 reagent utilized] |
| S1 | 2% Pyridine in acetonitrile |
| S2 | 0.1% Trifluoroacetic acid in water |
| S3 | Methanol |
| S4 | Dimethylformamide |

The C-terminal sequencer program summary is set forth in Table I. The PE-COOH bearing the YGGFL sample is placed in the reactor (CFR) of the sequencer depicted by FIG. 2. Sequencing is accomplished pursuant to the program set forth by Table 1. In this program, the CFR is always held at 70° C. and the CF (conversion flask) at 40° C.

To deliver the various reagents and solvents to the CFR a gentle pressure (1–3 atms) of argon is applied to each bottle. Argon was chosen because of its chemical inertness. Other suitable inert gases could be Helium and Nitrogen. Each bottle on the C-terminal instrument has its own pressure regulator (represented by the hexagon in the schematic). When it is time to deliver a reagent, a solenoid actuated valve is opened (in this case the Angar valve) in order to let the argon pass through the valve to the bottle. Since each bottle is sealed, the argon pressure pushes the solvent through the line at the bottom of each bottle to the valve block. There a solenoid actuated valve is opened to allow the solvent to flow into the valve block and on into the CFR. Once the CFR is full, the flow is stopped by closing the valves and the reaction is allowed to continue for the desired length of time. After the reaction, the Angar valve (BO CFR, blow out CFR) is opened to allow argon to pass through and on into the

TABLE I

| Continuous Flow Reactor (CFR) (70 C.) | Conversion Flask (CF) (35 C.) | Duration (sec) | Total Time (min) |
|---|---|---|---|
| R1 reaction | | 180 | |
| Dry | | 180 | |
| R2 reaction | | 450 | |
| R2 reaction | | 450 | |
| Blow out | | 15 | |
| S1 reaction | | 225 | |
| S1 reaction | | 225 | |
| Blow out | | 30 | |
| R1 reaction | | 180 | |
| Dry | | 180 | |
| R2 reaction | | 450 | |
| R2 reaction | | 450 | |
| Blow out | | 15 | |

TABLE I-continued

| Continuous Flow Reactor (CFR) (70 C.) | Conversion Flask (CF) (35 C.) | Duration (sec) | Total Time (min) |
|---|---|---|---|
| S1 reaction | | 225 | |
| S1 reaction | | 225 | |
| Blow out | | 60 | |
| R1 reaction | | 180 | |
| Dry | | 180 | |
| R2 reaction | | 450 | |
| Blow out | | 15 | |
| S1 reaction | | 225 | |
| Blow out | | 30 | |
| S3 rinse | | 120 | |
| S4 rinse | | 240 | |
| S3 rinse | | 120 | |
| S4 rinse | | 240 | |
| S3 rinse | | 120 | |
| S4 rinse | | 60 | |
| R3 reaction | | 1200 | |
| R3 to CF | | 30 | |
| R3 reaction | Dry | 300 | |
| R3 reaction | Dry | 300 | |
| S2 delivery | | 10 | |
| S2 reaction | | 120 | |
| S2 to CF | | 30 | |
| S2 delivery | | 9 | |
| S2 reaction | | 120 | |
| S2 to CF | | 30 | |
| | inject | 7 | |
| pause | pause | 60 | |
| Dry | Dry | | 100 | top of the valve block. This pushes the reagent or solvent in the CFR out to waste or to the CF, depending on which solenoid is actuated on the three way switching valve just after the CFR. The program for sequencing therefore consists of only opening and closing solenoid actuated valves at various times.

| C-TERMINAL SEQUENCER PROGRAM SUMMARY | | | |
|---|---|---|---|
| Continuous Flow Reactor (CFR) (70 C) | Conversion Flask (CF) (35 C.) | Duration (sec) | Total Time (min) |
| pressurize R1 | | 5 | |
| deliver R1 | | 25 | |
| R1 reaction | | 180 | |

In the first step, pressurize R1, means the Angar valve is opened for R1 and the R1 bottle is allowed to pressurize with R1 for 5 seconds. In the second step, deliver R1, the Angar valve for R1 is still open to maintain pressure on R1, but the solenoid on the reagent block for R1 is also opened, permitting R1 to flow into the CFR. Additionally, the solenoid on the 3-way switching valve is opened in order to permit equalization of pressure (this is a closed system) and to allow any overflow to go to a waste bottle. This flow is maintained for 25 seconds. At the end of 25 seconds, all of the solenoid actuated valves are closed and the R1 reagent, in this case 50% triethylamine in methanol is allowed to react with the covalently bound peptide for 180 seconds.

| blow out R1 | 180 sec |
|---|---|

This next step opens the Angar valve under the pressure regulator, BO CFR, allowing argon to flow into the top of the reagent valve block. The waste valve (3-way switching valve) just after the CFR is also opened. This permits the argon to push the contents of the CFR out to waste. In this case Argon is pushed through the CFR for 180 seconds and then all valves are shut off.

|  | Sec |
| --- | --- |
| R2 pressurize | 5 |
| R2 deliver | 3 |
| R2 reaction | 450 |
| R2 pressure | 5 |
| R2 deliver | 3 |
| R2 reaction | 450 |
| Blow out R2 | 15 |

The above series of steps occurred the same way as described for R1, but now R2 was used, so instead of opening and closing the valves for R1, the corresponding valves for R2 were used.

|  | Sec |
| --- | --- |
| S1 pressurize | 5 |
| S1 deliver | 10 |
| S1 rp-action | 225 |
| S1 pressurize | 5 |
| S1 deliver | 10 |
| S1 reaction | 225 |
| Blow out S1 | 30 |

As discussed in the explanation of the chemistry, the above sequence of events, treatment of the peptide with triethylamine, phosphoryl isothiocyanate reagent, and pyridine is repeated two more times in order to push the equilibrium all the way toward thiohydantoin formation.

|  | Sec |
| --- | --- |
| pressurize R1 | 5 |
| deliver R1 | 25 |
| R1 reaction | 180 |
| blow out R1 | 180 |
| R2 pressurize | 5 |
| R2 deliver | 3 |
| R2 reaction | 450 |
| R2 pressure | 5 |
| R2 deliver | 3 |
| R2 reaction | 450 |
| Blow out R2 | 15 |
| S1 pressurize | 5 |
| S1 deliver | 10 |
| S1 reaction | 225 |
| S1 pressurize | 5 |
| S1 deliver | 10 |
| S1 reaction | 225 |
| Blow out S1 | 30 |
| pressurize R1 | 5 |
| deliver Ri | 25 |
| R1 reaction | 180 |
| blow out R1 | 180 |
| R2 pressurize | 5 |
| R2 deliver | 3 |
| R2 reaction | 450 |
| R2 pressure | 5 |
| R2 deliver | 3 |
| R2 reaction | 450 |
| Blow out R2 | 15 |
| S1 pressurize | 5 |
| S1 deliver | 10 |
| S1 reaction | 225 |
| S1 pressurize | 5 |
| S1 deliver | 10 |
| S1 reaction | 225 |
| Blow out S1 | 30 |

At this stage 90% or greater of the peptide C-terminal amino acid is derivatized to a thiohydantoin. However there is still some isothiocyanate reagent and pyridine present in the CFR or in various lines that will add a lot of UV absorbing stuff to the HPLC chromatogram of the released thiohydantoin amino acid. The next few steps involve rinsing the covalently coupled peptide with methanol, DMF, methanol, DMF, methanol, followed by DMF again. Several other solvents could potentially be used for this purpose.

|  | Sec |
| --- | --- |
| S3 pressurize | 5 |
| S3 deliver | 120 |
| Blow out S3 | 20 |
| S4 pressurize | 5 |
| S4 rinse | 240 |
| S4 blowout | 20 |
| S3 pressurize | 5 |
| S3 deliver | 120 |
| Blow out S3 | 20 |
| S4 pressurize | 5 |
| S4 rinse | 240 |
| S4 blowout | 20 |
| S3 pressurize | 5 |
| S3 deliver | 120 |
| Blow out S3 | 20 |
| S4 pressurize | 5 |
| S4 rinse | 240 |
| S4 blowout | 20 |

The next step is the cleavage step. R3 (sodium trimethylsilanolate in methanol and t-butanol) is brought into the CFR, allowed to react for 1200 seconds and then instead of pushing the contents of the CFR into waste as with R1, R2, S1, S3 and S4 above, the contents of the CFR are pushed into the CF. Once in the CF the alcoholic solution containing the thiohydantoin is dried by blowing a stream of argon on it for 2×300 seconds. This is accomplished by opening the Angar valve under the AR to CF regulator. While this drying is occurring in the CF, the shortened peptide is being treated with sodium trimethylsilanolate in order to convert the silylated carboxylic acid group of the shortened peptide back into a free carboxylic acid group.

|  |  | Sec |
| --- | --- | --- |
| R3 pressurize |  | 5 |
| R3 deliver |  | 17 |
| R3 reaction |  | 1200 |
| R3 to CF |  | 30 |
| R3 pressurize |  | 5 |
| R3 deliver |  | 17 |
| R3 reaction | Dry | 300 |
| Blowout R3 |  | 20 |
| R3 pressurize |  | 5 |
| R3 deliver |  | 17 |
| R3 reaction | Dry | 300 |
| Blow out R3 |  | 20 |

At this point the dried thiohydantoin amino acid in the CF must be dissolved in injection solvent for injection into the HPLC. This is 0.1% trifluoroacetic acid (TFA) and is in solvent bottle 2 (S2). Since the R4 function, which would be capable of delivering a specific amount through a loop directly into the CF, does not work (electronic problem) the solvent is delivered through the CFR. It is delivered twice in order to deliver the proper volume for injection. Additionally, it was initially thought that aqueous TFA would convert the silylated carboxylic acid on the shortened peptide after cleavage to the free carboxylic acid so there is a 120 second reaction time of the peptide with the aqueous TFA still present.

|  | Sec |
| --- | --- |
| S2 pressurize | 5 |
| S2 delivery | 10 |
| S2 reaction | 120 |
| Blow S2 to CF | 30 |
| S2 pressurize | 5 |
| S2 delivery | 9 |
| S2 reaction | 120 |
| S2 to CF | 30 |

Injection into the HPLC is accomplished by applying argon pressure to the CF regulator (Blow out CF) and pushing the contents of the CF into the 100 μl HPLC injection loop. The pause step is 60 seconds long in order to allow the contents of the HPLC injection loop to run on the HPLC column. The last step involves flushing both the CFR and CF with Argon for 100 seconds in order to clean out the system. The whole cycle is then repeated as often as desired.

|  |  | Sec |
| --- | --- | --- |
|  | Inject | 15 |
| Pause | Pause | 60 |
| Dry | Dry | 100 |

The cycle time for the entire program takes approximately 2 and ½ hours.

Figure 3A:
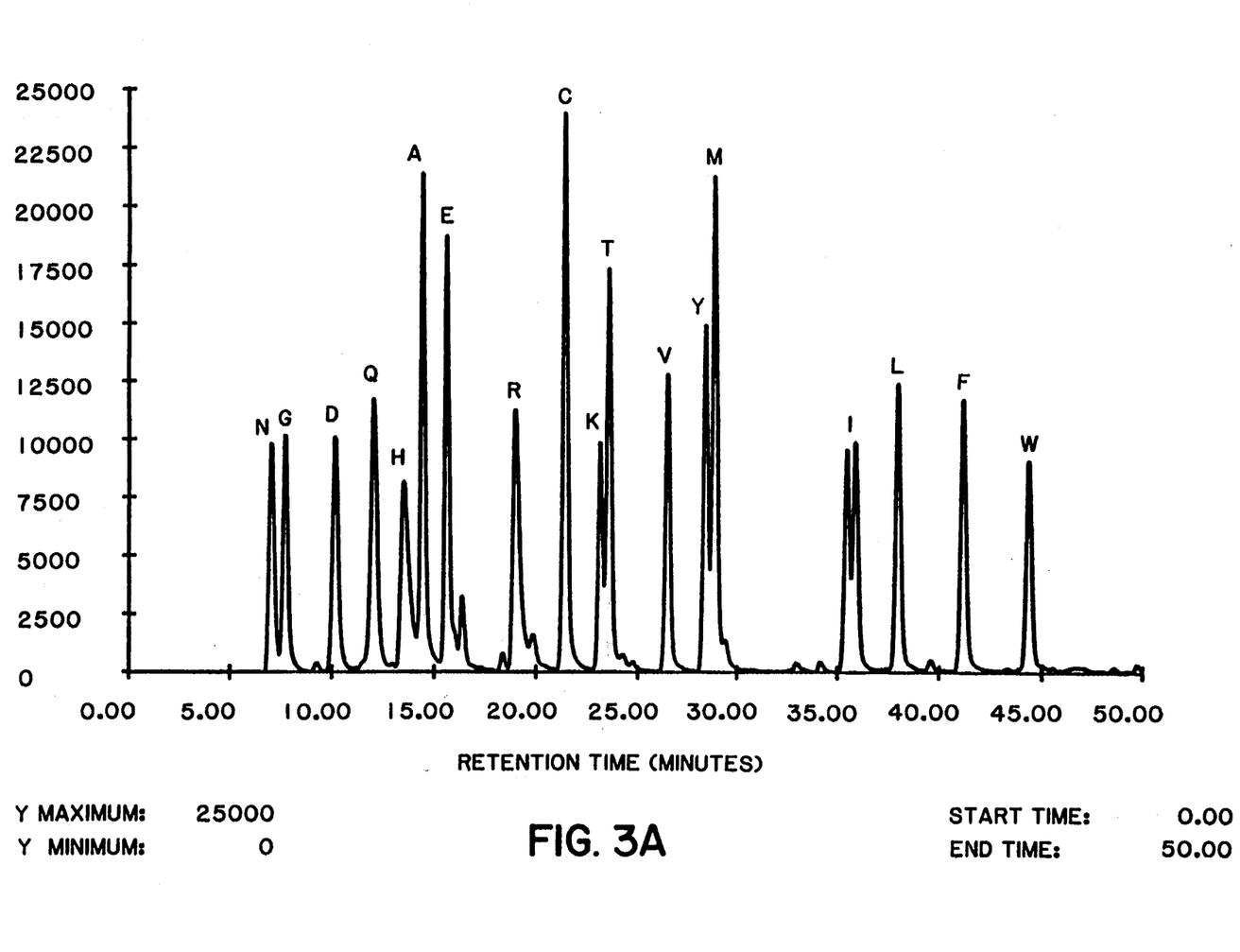
FIGS. 3A, 3B, 3C, 3D and 3E are a chromatogram depicting separation, in four cycles, of amino acid thiohydantoins from the peptide YGGFL utilizing the sequencer depicted by FIG. 2.
Figure 3B:
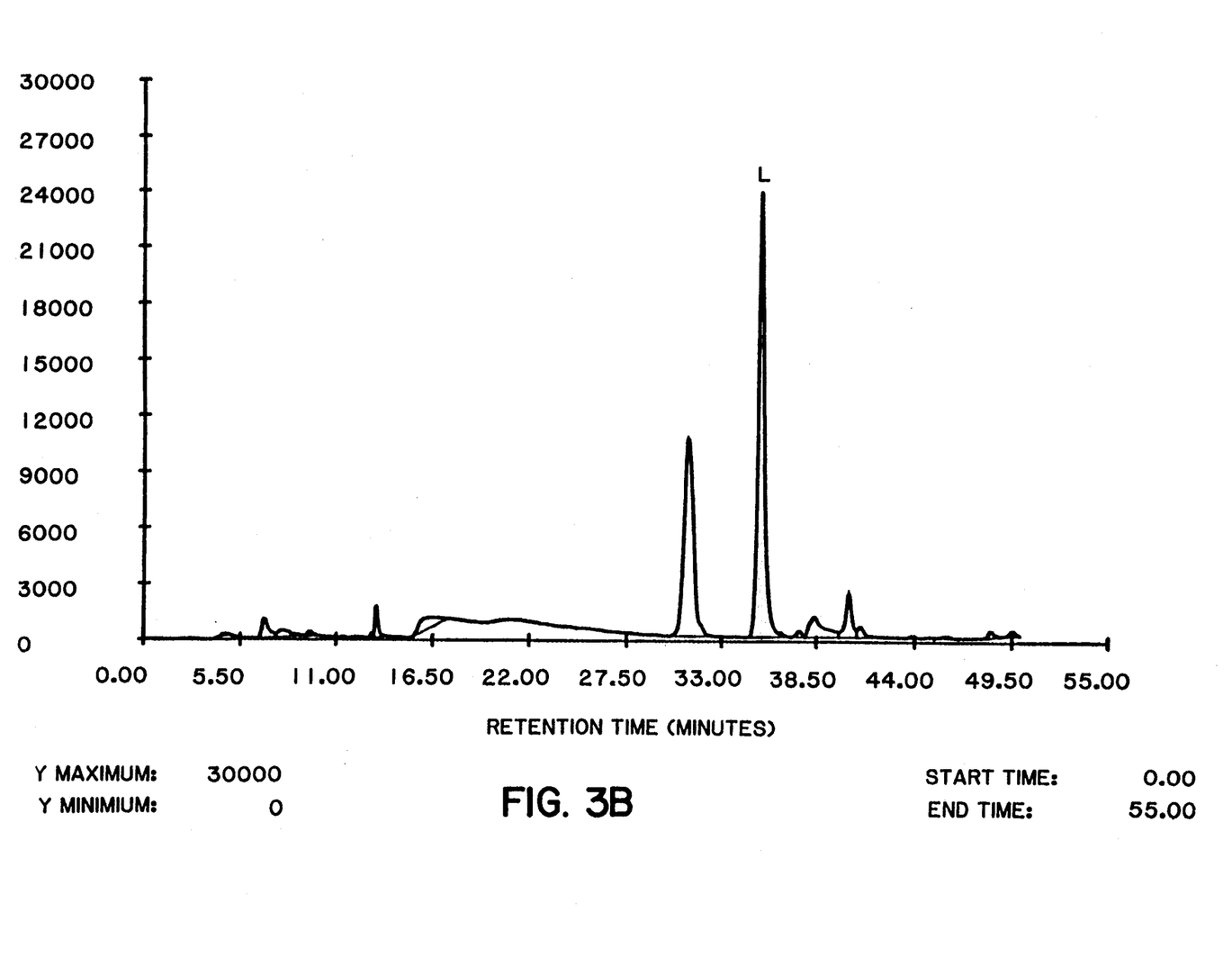
Figure 3C:
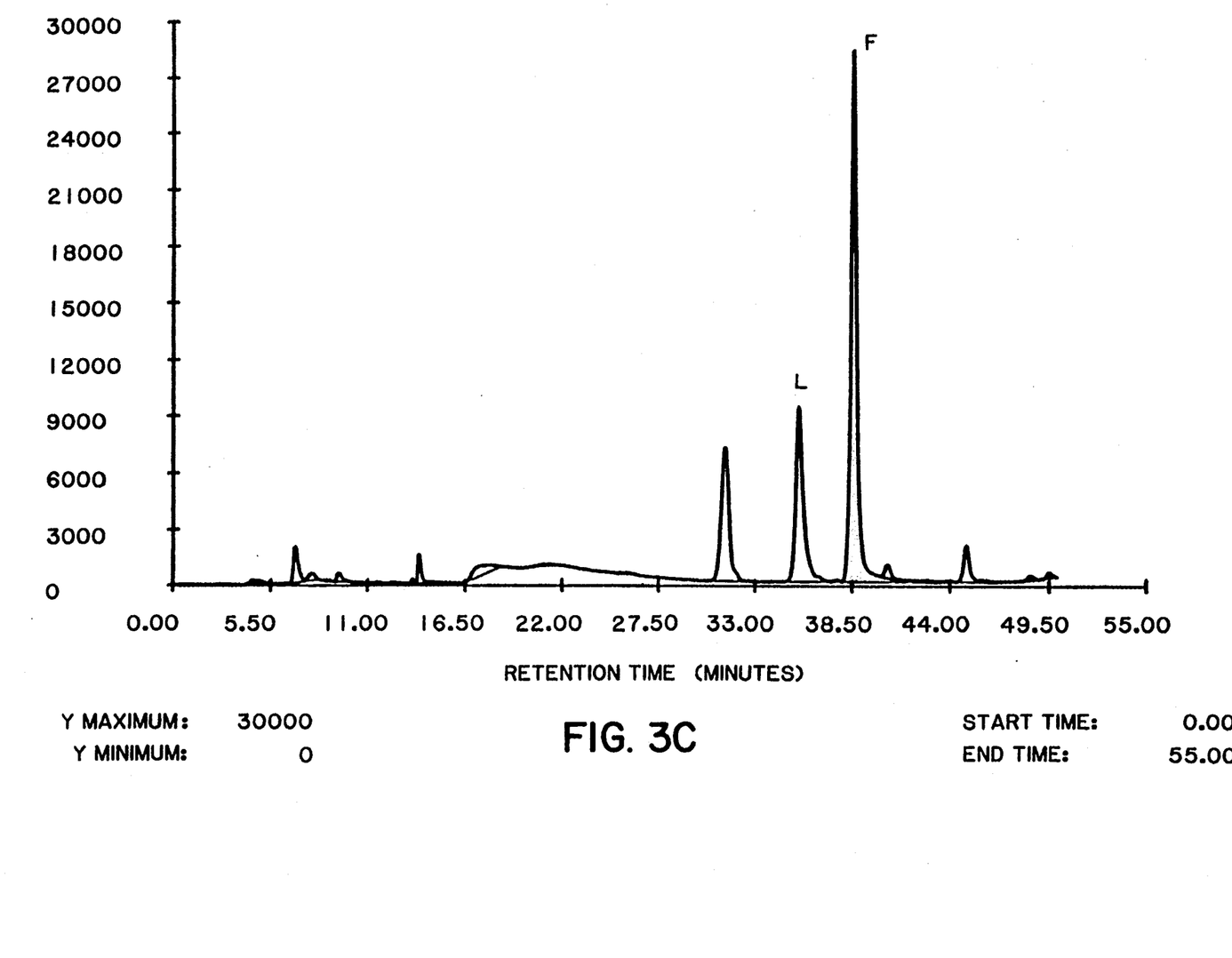
Figure 3D:
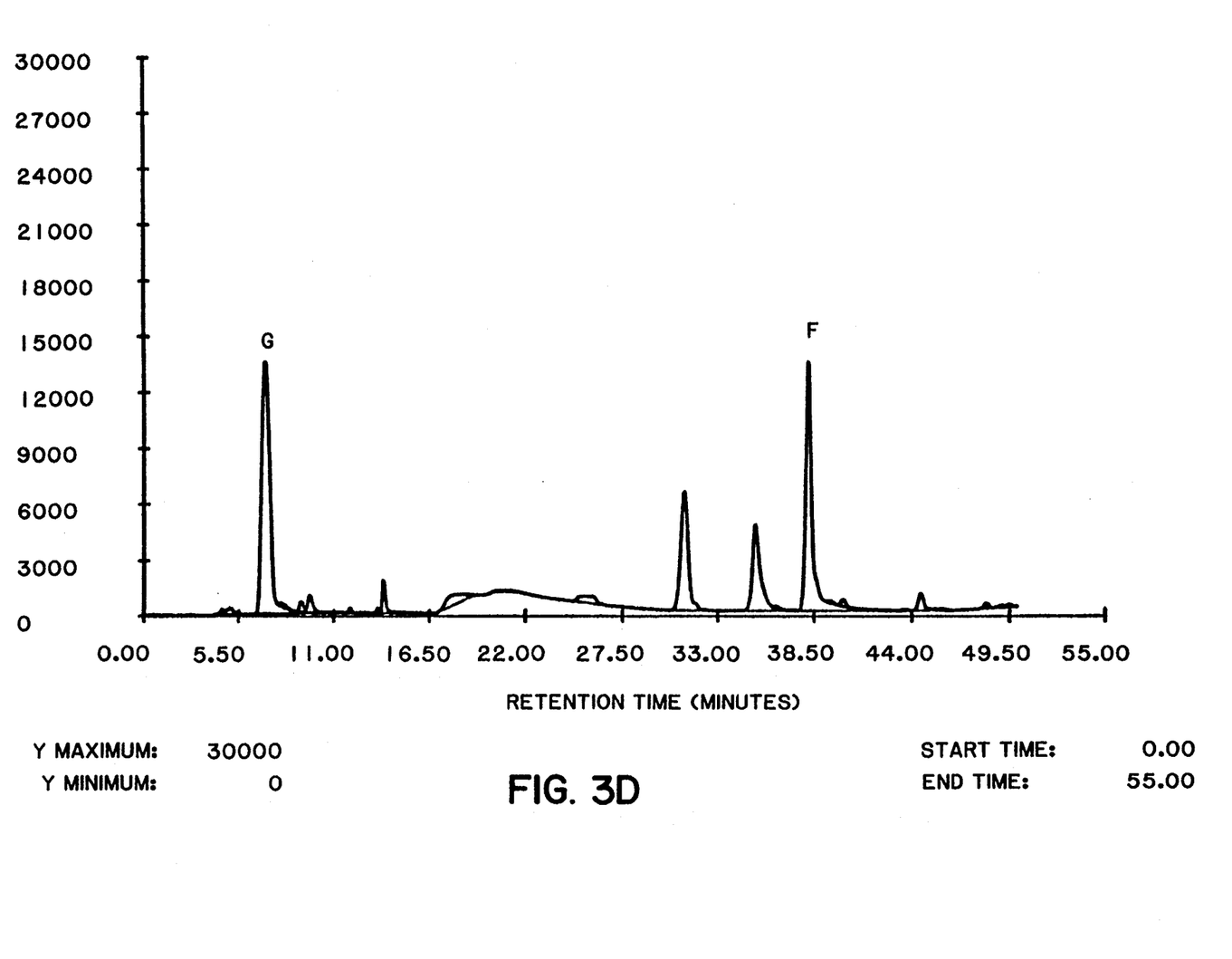
Figure 3E:
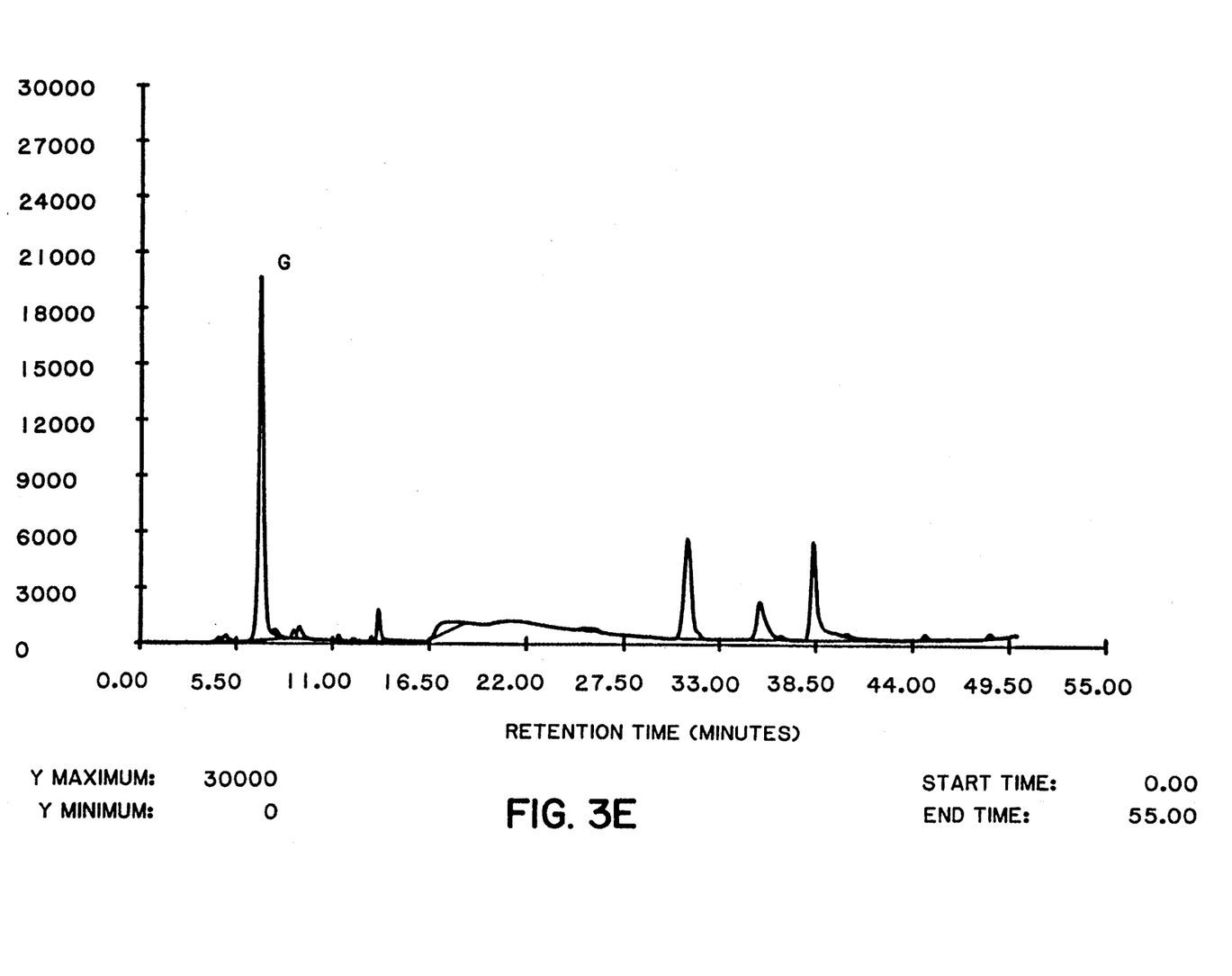

The product of the first cycle is subjected to HPLC as FIG. 2 indicates. FIG. 3A is the resulting first cycle chromatogram. FIGS. 3B, 3C, and 3D are chromatograms of the products of cycles 2, 3, and 4. In each case, the derivatized C-terminal amino acid is identified by retention time on a C-18 reverse phase HPLC column. The separation of the thiohydantoin amino acids was performed on a 2.1×250 mm Reliasil 3μ 100 Å column at 35° C. with a flow rate of 0.15 ml/min. Solvent A is 0.1% trifluoroacetic acid in water. Solvent B is 80% acetonitrile, 10% water, and 10% methanol. Gradient elution is performed as follows: 0% B for 2 min., 0–4% B for 35 min., and 35–50% B for 10 min. Absorbance is monitored at 265 nm.

Advantages of phosphoryl/pyridine chemistry over TMS-ITC/acetic anhydride include:

(1) Increased yields of sequencing. Typical initial yields with prior art TMS-ITC/acetic anhydride are 30%. Quantitative data is not ready yet, but sequencing chromatograms indicate initial yields are dramatically improved with this new chemistry.

(2) Precleavage is eliminated. The TMS-ITC/acetic anhydride chemistry often gave a preview amino acid. The amino acid from the next cycle was always present.

(3) Elimination of acetic anhydride. Proteins are widely known not to be soluble in acetic anhydride. The elimination of acetic anhydride is believed to therefore facilitate application of C-terminal sequencing to protein samples. Due to problems caused by the acetic anhydride activation the yields of sequencing were reduced for the amino acids Thr, Ser, Glu, and Asp. Two peaks were also generated on sequencing from both Lys and Thr due to partial acetylation of the amino acid side chains. So far, the sequencing yields of Asp have been shown to be dramatically improved with this new chemistry. It is anticipated that similar results will be obtained with Thr, Ser, Glu and Lys.

(4) UV absorbing background peaks which can interfere with identification of the released thiohydantoin amino acids are markedly reduced with the phosphoryl/pyridine chemistry as compared to the TMS-ITC/acetic anhydride chemistry.

We claim:

1. In a process for the carboxyl terminal sequencing of a polypeptide which involves the reaction of a carboxylate of said polypeptide with a phosphoroisothiocyanatidate to form a peptidyl isothiocyanate derivative of said carboxylate said peptidyl isothiocyanate derivative of said carboxylate having the phosphoryl moiety the improvement which comprises reacting said peptidyl isothiocyanate derivative with an amine to eliminate said phosphoryl moiety therefrom and produce a thiohydantoin moiety at the carboxyl terminal of said polypeptide.

2. The claim 1 process in which said amine reacted with said peptidyl isothiocyanate derivative is pyridine.

3. The claim 1 or claim 2 process in which said phosphoroisothiocyanatidate is phenylphosphoroisothiocyanatidate.

4. A process as defined by claim 1 or claim 2 in which said polypeptide is covalently attached to a membrane.

5. A process as defined by claim 1 or claim 2 in which said polypeptide sample is covalently attached to a carboxylic acid modified polyethylene support.

* * * * *